United States Patent [19]

Beilfuss et al.

[11] Patent Number: 5,756,500
[45] Date of Patent: May 26, 1998

[54] AQUEOUS DISPERSION HAVING A FUNGICIDAL AND ALGICIDAL EFFECT

[75] Inventors: Wolfgang Beilfuss; Heinz Eggensperger; Karl-Heinz Diehl; Peter Oltmanns, all of Hamburg, Germany

[73] Assignee: Schulke & Mayr GmbH, Norderstedt, Germany

[21] Appl. No.: 566,395

[22] Filed: Dec. 11, 1995

Related U.S. Application Data

[63] Continuation of Ser. No. 163,807, Dec. 8, 1993, abandoned.

[30] Foreign Application Priority Data

Dec. 8, 1992 [DE] Germany .................... 42 42 389.9

[51] Int. Cl.$^6$ .................... A01N 43/34; A01N 43/52; A01N 43/66; A01N 43/78
[52] U.S. Cl. .................... 514/245; 504/155; 504/156; 514/367; 514/395
[58] Field of Search .................... 514/245, 367, 514/395; 504/155, 156

[56] References Cited

U.S. PATENT DOCUMENTS

| | | | |
|---|---|---|---|
| 4,964,892 | 10/1990 | Hsu | 71/67 |
| 4,983,618 | 1/1991 | Pulido et al. | 514/367 |
| 5,093,344 | 3/1992 | Donofrio et al. | 514/367 |
| 5,125,953 | 6/1992 | Gattner et al. | 71/76 |

*Primary Examiner*—Allen J. Robinson
*Attorney, Agent, or Firm*—Fish & Richardson P.C.

[57] ABSTRACT

The invention relates to an aqueous dispersion which includes a mixture composed of the active ingredients carbendazime, 2-(thiocyanomethylthio)-benzothiazole and 2-methylthio-4-t-butyl-amino-6-cyclopropylamino-s-triazine. Further active ingredients with algicidal or fungicidal effect can optionally be present in the dispersion. The dispersion can be used for the fungicidal and algistatic finishing of paints, varnishes and plasters.

9 Claims, No Drawings

AQUEOUS DISPERSION HAVING A FUNGICIDAL AND ALGICIDAL EFFECT

This application is a continuation of application No. 08/163.807, filed on 8 Dec. 1993, now abandoned.

The invention relates to aqueous dispersions for the biocidal finishing of objects or coatings whose surfaces are, experience shows, frequently attacked by algae or fungi. It further relates to a process for their production and their use.

Algal and fungal attack is not only not very attractive optically but, in the event of subsequent lichen or moss growth, can also lead to material damage and a reduction in service life. Microbial attack on objects or coatings applied to them occurs particularly intensively in fields with high atmospheric moisture, for example in the field of the food industry, in dairies, breweries or on the north side of buildings. Particularly affected are coatings such as paints, varnishes and plasters.

The attempt to solve the problem described above by adding powdered substances to the coating materials used is associated with numerous industrial application disadvantages. The requirement for solvent-free or low-solvent preparations has led to the development of aqueous dispersions in which known water-insoluble fungicidal and algistatic active ingredients were used. Particularly problematical is the treatment of Alternaria species which frequently occur despite fungicidal and algistatic finishing of, for example, coatings on paint, varnish and plaster coats with standard commercial preparations. The dispersions available on the market show no specific effectiveness against Alternaria. Stable, effective aqueous dispersions for the fungicidal and algistatic finishing of paints and varnishes and plasters with Alternaria effectiveness with simultaneous good stability and wash-out resistance are, as yet, not available.

It is therefore the object of the invention to make available an aqueous dispersion with fungicidal and algistatic effectiveness, including effectiveness against Alternaria species, which satisfactorily eliminates the disadvantages mentioned above.

This object is solved by an aqueous dispersion which is characterized in that it comprises a mixture of the active ingredients a) carbendazime, b) 2-(thiocyanomethylthio) benzothiazole (TCMTB) and c) 2-methylthio-4-t-butylamino-6-cyclopropylamino-s-triazine.

Preferred embodiments are the subject of the dependent claims.

The dispersion according to the invention is distinguished in particular by its good microbiological effectiveness against fungi (specially Alternaria species) and algae. This biocidal action can even be achieved with high wash-out loading over an extended period of time. Compared with the individual components there is therefore not only a broader effect spectrum, but a synergistic effect increase is also displayed.

The dispersion according to the invention is distinguished overall by the following features:

wash-out resistance use of AOX-free additives and active ingredients (AOX adsorbable organic halogen compounds)

free from low boiling organic solvents use of the lowest possible proportions of organic solubilizers good to very good dispersion stability homogeneous mixture with good flow properties practically no sedimentation on storage good fastness to light, in particular UV light, pH, temperature and environmental influences good compatibility with other formulation components good process ability of the active ingredients good stability of the active ingredients in the preparation and in the worked-in product hydrolysis resistance of the active ingredients long-lasting effect at low use concentration low toxicity vis-a-vis mammals favorable price/performance ratio practically colorless and low in odor low vapor pressure of the active ingredients.

The essential feature is that the dispersion according to the invention is an active ingredient combination of the two fungicidal active ingredients: carbendazime and 2-(thiocyanomethylthio)benzothiazole (TCMTB) and the algistatic active ingredient: 2-methylthio-4-t-butylamino-6-cyclopropylamino-s-triazine.

It generally includes 1 to 99 wt. % of these active ingredients, the remainder of the dispersion consisting of normal formulation auxiliaries. The active ingredient content is preferably in the range from 2 to 90 wt. % and particularly preferably in the range from 5 to 80 wt. %.

The dispersion according to the invention includes, for example,

| | |
|---|---|
| 2.5 to 26 wt. % | carbendazime, |
| 6.6 to 69 wt. % | 30% aqueous emulsion of 2-(thiocyanomethylthio)-benzothiazole (TCMTB 30) and |
| 0.5 to 5 wt. % | 2-methylthio-4-t-butylamino-6 cyclopropylamino-s-triazine. |
| It preferably contains | |
| 10 to 40 wt. % | TCMTB 30 and |
| 1 to 3 wt. % | 2-methylthio-4-t-butylamino-6-cyclopropylamino-s-triazine. |

As well as the three active ingredients necessarily present according to the invention, one or more further algistatic and/or fungicidal active ingredients can also be present. These are preferably halogen-free and include, for example, the active ingredients thiabendazole, mercaptobenzthiazole and N-octylisothiazolone. Of these, thiabendazole is preferred. They can each be present in a quantity of up to 10 wt. %, their total quantity not exceeding 30 wt. %, however. Standard commercial pot preservatives such as for example O-formals, N-formals (formaldehyde depot compounds in which formaldehyde is reversibly bonded with alcohols such as ethylene glycol, propylene glycol, benzyl alcohol or butyl diglycol or with amine compounds such as ethanolamine and propanolamine with formation of hemiacetals or analogous compounds) or isothiazolones can also be added by choice to the dispersion. In the dispersion according to the invention the pot preservative can be contained in a quantity of 0.005 to 0.5 wt. %, preferably 0.01 to 0.1 wt. %. If the dispersions are used in a paint or another product, the quantity of the former can be raised beforehand to 2 wt. % or even up to 5 wt. %. No additional pot preservative then needs to be added to the paint itself.

As well as the active ingredients, the dispersion according to the invention can further include usual auxiliaries such as dispersion agents, high-boiling solubilizers, anti-caking agents, thickening agents, defoaming agents, low-temperature stabilizers, fillers, preservatives and/or carriers.

Suitable as dispersion agents are for example non-ionic surfactants such as fatty alcohol ethoxylates, Alkylphenol ethoxylates in which the alkyl group includes 1 to 15 carbon atoms, particularly 1 to 10 carbon atoms and the number of ethylenoxy groups is 1 to 10, and polyacrylic acid salts are also usable. Particularly suitable is, for example, $C_{10}$ oxoalcohol with 3 ethylenoxy groups, $C_{13}$ oxoalcohol with 3 or 5 ethylenoxy groups, $C_{12}$–$C_{14}$ fatty alcohol with 2.5 ethylenoxy groups, lauryl alcohol polyglycol ethers with 3 ethylenoxy groups and nonyl phenol with 5 ethylenoxy groups. These dispersion agents can each be used alone or in a mixture of one or more of these compounds. Non-ionic fatty alcohol ethoxylates with 2 to 9 ethylenoxy groups are preferred. The dispersion agents can be used in a quantity of up to 30 wt. %, particularly up to 20 wt. % and preferably 14 to 18 wt. %.

Examples of high-boiling solubilizers are glycols, their esters or ethers such as ethylene glycol, diethylene glycol, polyethylene glycol (300 to 600 Dalton) or their mono- or dialkyl ethers, propylene glycol, dipropylene glycol, polypropylene glycol, their mono- or dialkyl ethers, butylene glycol, dibutylene glycol, their mono- or dialkyl ethers or the corresponding alkyl esters, the alkyl groups each having 1 to 10 and preferably 1 to 4 carbon atoms. Particularly preferred are 1,3-butylene glycol and polyethylene glycol 400 (the average molecular weight is 400). Mixtures of these solubilizers can also be used. In some cases the solubilizers in the dispersions have a consistency regulating (thickening or diluting) effect and/or act as low temperature stabilizers (antifreeze). The solubilizers can be used in a quantity of up to 15 wt. %, particularly up to 10 wt. % and preferably up to 8 wt. %. Quantities of 4 to 8 wt. % are particularly preferred.

Preferred mixtures of dispersion agents and solubilizers include:

| | |
|---|---|
| 10 wt. % | $C_{13}$ oxoalcohol with 5 ethylenoxy groups |
| 4–8 wt. % | laurylalcohol polyglycol ether with 3 ethylenoxy groups (preferably 6 wt. and |
| 4–8 wt. % | butanediol-1,3 or of a mixture of butanediol-1,3 and polyethylene glycol 400 (preferably 6 wt. %) or |
| 6–8 wt. % | polyethylene glycol 400 (preferably at least 4 wt. %). |

In particular, the stability and handling properties of dispersions containing such dispersion agents and/or solubilizers is surprisingly good even after prolonged storage, even under very unfavorable temperature and moisture conditions. As a rule, demulsification of the dispersion components is even avoided.

The active ingredient combination according to the invention can be present in the form of a powder, a solution or a paste, being preferably flowable.

The individual components of the dispersion preferably have a particle size <70 μm, a particle size <60 and in particular <50 μm being preferred. Such a particle size can be obtained by very fine grinding of the solid active ingredient components. Grinding is preferably carried out in the wet state using pearl and/or ball and/or colloid mills.

The dispersions according to the invention can be produced according to the usual processes familiar to the expert. They are, for example, produced by very fine milling of the solid active ingredient components in the presence of the other formulation auxiliaries in water to a premix followed by stirring in of the 7 liquid active ingredient components. Thus, for example, the active ingredient components 2-methylthio-4-t-butyl-amino-6cyclopropylamino-s-triazine and carbendazime can be very finely milled wet first of all and then the third active ingredient TCMTB stirred in.

The dispersion according to the invention can be used as a biocidal additive to coatings, to plastic dispersions, in particular those which are film-forming and based on polyacrylate, for the treatment of surfaces and materials and for the fungicidal and algistatic finishing of paints, varnishes and plasters.

In practice the concentration of the dispersion according to the invention used can be in the range from 0.05 to 10 wt. %, particularly 0.1 to 5 wt. % and preferably 0.5 to 3 wt. %.

In coatings, the dispersion according to the invention can be used in quantities such that 0.01 to 10 g, preferably 0.1 to 4 g, are used per 1 $m^2$ surface area.

The effectiveness of the dispersion according to the invention can be shown by means of the inhibition zone test.

In this, the effectiveness of homogeneous clear solutions of the individual active ingredients and of the active ingredient combination according to the invention is tested in dimethyl formamide as solvent. An increase in effect is to be observed with yeast and fungi on using the active ingredient combination.

To check the fungicidal and algistatic effectiveness of the dispersions according to the invention in products finished with it, the following formulations A and B were worked into a white standard dispersion paint. It was the aim to check these formulations compared with a known product C for their microbiological effectiveness against fungi (specially Alternaria) and algae without and following washout loading. In addition, the finished samples were to be judged in another test mixture as regards possible discoloration by weathering influences.

| | Formulation A |
|---|---|
| 26 wt. % | carbendazime |
| 69 wt. % | TCMTB 30 |
| 5 wt. % | 2-methyl-4-t-butylamino-6-cyclopropyl-amino-s-triazine |
| | Formulation B |
| 10 wt. % | carbendazime |
| 26.9 wt. % | TCMTB 30 |
| 3.3 wt. % | 2-methylthio-4-t-butylamino-6-cyclopropyl-amino-s-triazine |
| | Formulation C |
| 5 wt. % | carbendazime |
| 20 wt. % | 3-(3,4-dichlorophenyl)-1,1-dimethyl urea |

Materials and Methods

The pure acrylate facade coating used for the tests had the following composition:

| | Wt. % |
|---|---|
| Texanol | 1.20 |
| Natrosol 250 HBR | 0.30 |
| Water | 19.95 |
| Calgon N, 10% in water | 0.20 |
| Pigment distributor A | 0.25 |
| Defoaming agent Nopco 8034, 50% in water | 0.12 |
| Ammonia, 25% | 0.50 |
| Titanium dioxide Kronos RN56 | 20.00 |
| Durcal 5 | 10.00 |
| Millicarb | 10.40 |
| Aluminum silicate P 820 | 2.00 |
| Plextol D 498 | 35.00 |
| Defoaming agent Nopco 8034 | 0.08 |

1.0% each of the known product C, A or B were worked into this coating material in 3 separate mixtures. The three mixtures were for—.

a) testing for discolorations b) testing for resistance to fungal and algal attack without wash-out loading c) testing for resistance to fungal and algal attack with washout loading.

A and B represent very finely wet-milled active ingredient combinations according to the invention of the two fungicidal and the one algistatic active ingredient(s). Compared with A, B has improved flow properties. After intensive stirring of the samples, the latter were applied with a film-coating triangle in 250 μm wet film thickness on filter board (type 2589 wet-strength) as carrier material.

The test objects were predried for 24 hours at room temperature and then post-dried for 24 hours at 40° C.

The test objects of mixture a) were exposed to artificial, intensified weathering (bedewing, UV) (QUV, Q-Panel Comp., Cleveland) for 500 hours to test for possible discoloration through environmental and light influences, and evaluated directly afterwards. Mixtures b) and c) were subjected to microbiological testing. The test objects of mixture c) were subjected to wash-out loading through flowing water (ca. 1 l/min) for 72 hours and then dried as described above. The dried test objects were irradiated with UV for 24 hours (3 tubes, Philips TUV 40 W 640 T 12, 50 cm away from the test pieces).

Test pieces having a diameter of 50 mm were punched out from the center of the test objects and then sterilized with gamma rays.

Testing for Resistance to Fungal Attack

The fungi *Penicillium funiculosum*, *Aspergillus niger* and Alternaria sp. were used as test organisms.

0.2 ml of a spore suspension with a spore quantity of ca. $10^7$/ml were spread on Sabouraud's agar. The test pieces (φ50 Mm) were placed on the thus-prepared agar and incubated for 2 weeks at 25° to 27° C.

Appraisal criteria in the evaluation were the fungal growth on the plate or the testpieces and an inhibition zone formation around the testpieces. The evaluation was semi-quantitative.

Testing for Resistance to Algal Attack

The green algae Chlorella fusca was used as test organism.

0.1 ml of an algae suspension with a concentration of ca. $10^6$ cells/ml were spread on a mineral medium agar (Knop's solution +0.9% agar-agar). The test pieces with a diameter of 50 mm were spread on the thus-prepared agar. 0.3 ml algae suspension were then additionally distributed uniformly onto the surface of the test pieces. Incubation took place at 25° C. under intensive illumination (2000 lux; 4x Philips TLD 18W). The test pieces were kept continually moist throughout the one--week incubation period.

Appraisal criteria in the evaluation were the inhibition zone around the test pieces and the algal growth on the surface of the test pieces. The evaluation was semi-quantitative.

Results

A combined dew/UV weathering of 500 hours did not lead to any discoloration of the colored films.

The effectiveness against Penicillium funiculosum of all the preparations tested was sufficient even after a 72-hour exposure to thwart a surface growth on the test pieces.

The wash-out resistance of A and B was generally better than that of the known product.

A and B showed a very good effectiveness against Alternaria sp. which, at a use concentration of 1.0%, was completely maintained even after a wash-out loading of 72 hours.

The good effectiveness of these two preparations against algae corresponded to that of the known product and was maintained with a use concentration of 1.0% even after a wash-out loading of 72 hours.

The results are summarized in tables 1 and 2.

TABLE 1

Resistance of a facade paint to fungal attack, inhibition effect on *Aspergillus niger* and Alternaria sp

| | Aspergillus niger | | Alternaria sp | |
| | Wash-out loading | | | |
| | 0 h | 72 h | 0 h | 72 h |
| Control | 5 | 5 | 5 | 5 |
| C 1.0% | 1 | 2 | 5 | 5 |
| A 1.0% | (0) | 1 | 2 | 2 |
| B 1.0% | (0) | 1 | 2 | 2 |

0 = Zone formation (growth-free zone in the area around the sample)
(0) = Fungus has grown as far as the sample
1 = Sample overgrown only on the rim
2 = Sample overgrown in from rim (less than 25%)
3 = Sample surface overgrown with individual colonies (25–75%)
4 = Sample surface widely overgrown (> = 75%)
5 = Sample surface completely overgrown (100%)

TABLE 2

*Chorella fusca*

| | Wash-out loading | | | |
| | 0 h | | 72 h | |
| | Inhibition zone | Growth | Inhibition zone | Growth |
| Control | 0 | +++ | 0 | ++ |
| C 1.0% | >18 mm | – | 16 mm | + |
| A 1.0% | 16 mm | – | 17 mm | – |
| B 1.0% | 17 mm | – | 16 mm | – |

– = no growth on the surface of the test piece
+ = slight growth on the surface of the test piece
++ = moderate growth on the surface of the test piece
+++ = massive growth on the surface of the test piece
0 = no zone of inhibition

We claim:

1. An aqueous fungicidal and algistatic synergistic effective amount of dispersion comprising a mixture of active ingredients comprising (a) from 2.5 to 26 wt. % percent of carbendazime, (b) from 6.6 to 69 wt. % of a 30% aqueous emulsion of 2-(thiocyanomethylthio)-benzothiazole, and (c) from 0.5 to 5 wt. % of 2-methylthio-4-t-butylamino-6-cyclopropylamino-s-triazine.

2. An aqueous dispersion according to claim 1 which comprises (a) from 5–10 wt. % of carbendazime, (b) from 10 to 40 wt. % of a 30% aqueous emulsion of 2-(thiocyanomethylthio)-benzothiazole, and (c) 1 from to 3% of 2 methylthio-4-t-butylamino-6-cyclopropylamino-s-triazine.

3. A dispersion according to claims 1 or 2, which additionally comprises pot preservatives selected from the group consisting of O-formals, N-formals, isothiazolones and mixtures thereof.

4. A dispersion according to claims 1 or 2 which additionally comprises one or more auxiliary components selected from the group consisting of dispersing agents, high-boiling solubilizers, anti-caking agents, thickeners, defoaming agents, low-temperature stabilizers, fillers, preservatives and carriers.

5. A dispersion according to claim 4 which comprises a dispersing agent selected from the group consisting of fatty alcohol ethoxylates alkyl phenol ethoxylates, in which the alkyl group has from 1 to 15 carbon atoms and the number of ethylenoxy groups is 1 to 10, polyacrylic acid salts and mixtures thereof.

6. A dispersion according to claim 4 which comprises high-boiling solubilizers selected from the group consisting of glycols, their esters and their ethers.

7. A dispersion according to claim 1 or 2 wherein the components of the dispersion each have a particle size smaller than 70 µm.

8. A dispersion according to claim 7 wherein the components each have a particle size smaller than 60 µm.

9. A dispersion according to claim 8 wherein the components each have a particle size smaller than 50 µm.

* * * * *

UNITED STATES PATENT AND TRADEMARK OFFICE
CERTIFICATE OF CORRECTION

PATENT NO.   : 5,756,500
DATED        : 26 May 1998
INVENTOR(S)  : Wolfgang BEILFUSS; Heinz EGGENSPERGER;
               Karl-Heinz DIEHL; and Peter OLTMANNS It is certified that error appears in the above-identified patent and that said Letters Patent is hereby corrected as shown below:

In Claim 1, line 1, insert after "algistatic" the words --dispersion comprising--.

In Claim 1, line 2, after the words "amount of", delete the words "dispersion comprising".

Signed and Sealed this

Thirteenth Day of October 1998

Attest:

BRUCE LEHMAN

Attesting Officer

Commissioner of Patents and Trademarks